United States Patent [19]

Yagashita et al.

[11] Patent Number: 4,980,631
[45] Date of Patent: Dec. 25, 1990

[54] METHOD FOR MEASURING THE SURFACE AREA OF BODIES

[76] Inventors: Aisaburo Yagashita, 5-2, Shinpocho 4 chome, Chigusa-ku, Nagoya-shi, Aichi 464; Takeo Oki, 39, Tennodori 3 chome, Tsushima-shi, Aichi 496, both of Japan

[21] Appl. No.: 381,915

[22] Filed: Jul. 19, 1989

Related U.S. Application Data

[63] Continuation-in-part of Ser. No. 301,528, Jan. 23, 1989, abandoned, which is a continuation of Ser. No. 23,943, Mar. 10, 1987, abandoned.

[51] Int. Cl.$^5$ .............................................. G01N 27/22
[52] U.S. Cl. .................................. 324/71.1; 324/658; 204/400
[58] Field of Search ............... 324/438, 439, 444, 450, 324/71.1, 62, 658, 691; 204/1 T, 400, 434

[56] References Cited

U.S. PATENT DOCUMENTS 3,649,472  3/1972  Morrissey et al. .................. 204/1 T
4,129,480  12/1978  Robert ............................... 204/1 T

FOREIGN PATENT DOCUMENTS 2303717  8/1974  Fed. Rep. of Germany ...... 204/1 T

Primary Examiner—Reinhard J. Eisenzopf
Assistant Examiner—Jack B. Harvey
Attorney, Agent, or Firm—Lowe, Price, Le Blanc, Becker & Shur

[57] ABSTRACT

A method for measuring the surface area of an electrically surface-conductive body comprises applying an a.c. voltage between the body and a corrosion-resistant opposite electrode, both being immersed in an electrically conductive solution having no corrosive influence upon the surface of the body. An electric capacity value for the body is obtained. The measured value is inserted in the function of a surface area and a similar measurement or value obtained using another body having a known surface area in a similar manner. If the body to be treated does not exhibit surface conductivity, the body may be coated on the surface with a conductive material.

2 Claims, 1 Drawing Sheet

METHOD FOR MEASURING THE SURFACE AREA OF BODIES

RELATED APPLICATIONS

This application is a continuation-in-part of application Ser. No. 07/301,528 filed Jan. 23, 1989, which is a continuation of application Ser. No. 07/023,943 filed Mar. 10, 1987, both now abandoned.

FIELD OF THE INVENTION

The present invention relates to a method for measuring the surface area of a body, the profile of which is not simple. More particularly, the invention relates to a surface area-measuring method useful in applying precision processings such as electrodeposition to the surface of such a body.

BACKGROUND OF THE INVENTION

Recent increased high-performance of machinery and corresponding demands for precision processing of the parts involved require that the surface treatment of various articles be of higher precision. Especially when it is intended to carry out various surface treatments such as electroplating, electrodeposition and anodizing with enhanced precision, it is desired to know in advance the surface area of the article to be treated for the purpose of achieving high efficiency.

The surface area of articles have hitherto been determined by calculation from the dimensions thereof, the thickness and amount of deposits applied thereon by electrodeposition or electroplating, and so on. However, such deterination has left much to be desired, since it has been time consuming and laborious as well as of less accuracy.

For that reason, inefficient procedures have often been applied, in which the surface area is visually determined to carry out surface treatment tests which are repeatedly performed through trial and error until satisfactory results are obtained.

SUMMARY OF THE INVENTION

An object of the present invention is to provide a method for measuring with higher accuracy and speed the surface area of an article, the profile of which is not simple, and to provide a surface area-measuring method which can easily and readily be carried out without the skill needed in the prior art methods.

BRIEF DESCRIPTION OF THE DRAWINGS

The aforesaid and other objects and features of the present invention will become apparent from the following detailed description with reference to the accompanying drawings, which are provided for illustration alone, and in which.

DETAILED DESCRIPTION OF THE PREFERRED EMBODIMENTS

In carrying out the surface area-measuring method of the present invention, if the body to be measured exhibits surface conductivity, then it may be used without making any modification thereto. If the body to be measured has no surface conductivity, then it may be coated on the surface with a conductive material. An a.c. voltage is applied between the body and an opposite electrode which are immersed in an electrically conductive solution having no corrosiveness upon the body in order to measure an electric capacity value. Another body having a known surface area is separately used to carry out a similar measurement in order to obtain the function of surface area electric capacity value. With this function, the surface area of the body is determined from the aforesaid values.

Figure 1:
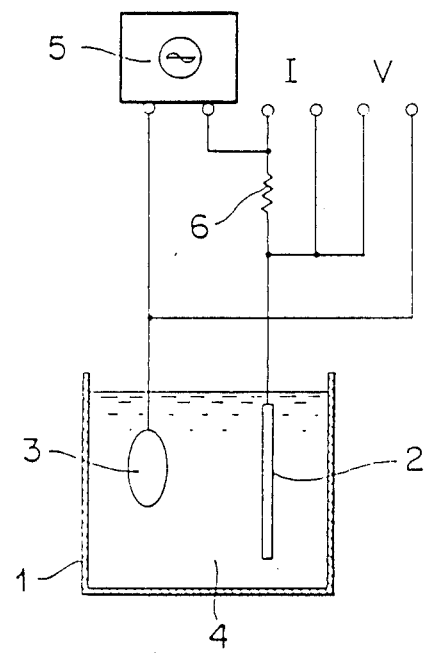
FIG. 1 is a view illustrating the arrangement for carrying out the method of the present invention.

An arrangement for carrying out the measuring method of the present invention is constructed as shown in FIG. 1.

A measuring vessel 1 is provided therein with a corrosion-resistant opposite electrode 2, and is filled therein with an electrically conductive solution 4. An electrically surface-conductive body 3 provided in advance with an electric wire is immersed in the conductive solution, and an alternating voltage is applied between the body 3 and the electrode 2 from an a.c. power source 5.

The voltage value between the body 3 and the electrode 2 is drawn out of V, while an alternating current flowing between the body 3 and the electrode 2 is drawn out of I, for example, as the alternating current intensity value appearing across a resistor 6, both being then recorded as the measurements. From these values, the electric capacity value is calculated.

While not so limited, the corrosion-resistant opposite electrode used in the present invention is preferably formed of a corrosion-resistant material such as titanium, platinum or carbon. However, use may be made of any suitable material which does not undergo electrolysis in the conductive solution. It is also preferred that the opposite electrode has a surface area sufficiently larger than that of the body to be measured.

The electrically conductive solution used is preferably of reduced corrosiveness and increased electrical conductivity, and is exemplified by about 1 to 30% aqueous solutions of salts such as sodium sulfate, sodium chloride and sodium carbonate, acids such as sulfuric acid and oxalic acid and bases such as natrium hydroxide and barium hydroxide.

If the body to be measured is formed of a metallic material, a surface treatment is not always needed. If that body is considered to be of insufficient surface conductivity, however, it is then required that electrical conductivity be afforded t the surface thereof by suitable methods such as electroless plating of metals such as copper, silver or nickel. It is noted that another body to be used for determination of the function of surface areas and electric capacity value should be coated on the surface with the same conductive material in the same manner. This is because, for instance, the relation between the area and the electric capacity value of the surface of a copper-plated body is different from that of an iron-plated body.

Several bodies having known but different surface areas are all subjected to similar surface-conducting treatment by means of electroless copper-plating, for instance. With the arrangement as mentioned above, thereafter, an alternating voltage is applied between the object to be measured and each opposite electrode to measure an electric capacity value.

Suitably, the frequency of the alternating voltage to be applied ranges from about 200 Hz to 50 KHz with the peak value being between about 1 mV and 100 mV, for instance.

The alternating current flowing between the body and the opposite electrode is then determined depending upon the electrical double-layer capacity—Cx—of the surface of the body, the electrical double-layer capacity—Cc—of the surface of the opposite electrode, the overall impedance including a resistant—R—of the conductive solution and the voltage—V13 applied as well as the frequency—W. Now, if the surface area of the body to be measured is allowed to be within a range exceeding largely that of the opposite electrode, while a well-conductive solution is used, the influence of Cc upon the electric capacity value is then so negligible that the electric capacity measured value—C—is considered to be approximately proportional to Cx.

Since the body has been subjected on the surface to uniform conducting treatment, the electrical double-layer capacity—Cx—of the surface of the body is considered to be proportional to the surface area—Sx—of the body. Thus, the surface area is proportional to the electric capacity value—C—, and may eventually be expressed in terms of $$C = K_1 Cx = k_1 Sx \qquad (1)$$

Figure 2:
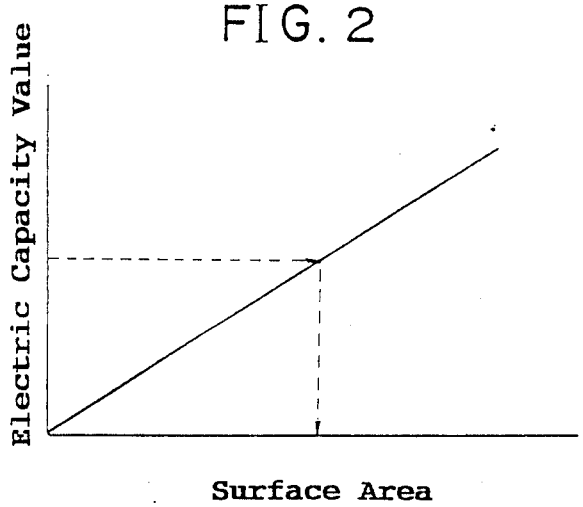
FIG. 2 is a graph showing the functional relation between the measurements and the surface areas.

Accordingly, the surface area of the body can be determined by obtaining a graph, as shown in FIG. 2, of the functional relation between Co and Sx from the electric capacity of another body having a known surface area or finding the proportionality factor—$k_1$ of the above equation (1) and substituting that measured electric capacity value of the body having an unknown surface area for the electric capacity value in the graph of FIG. 2, or substituting it for the electric capacity value in the above equation (1). In the present disclosure, it is noted that the wording "substitution" refers to the substitution of a measured value such as the electric capacity value for the purpose of determining an unknown surface area with the use of equations, tables or graphs showing such a functional relation as mentioned above.

The method of the present invention is demonstrated by the following examples:

EXAMPLE 1

A copper plate having a surface area of 30 cm$^2$ as the opposite electrode, and a 1-liter aqueous solution of 0.5 moles of sodium sulfate as the electrically conductive solution were placed in the vessel. An alternating current having a frequency of 1 KHz and a peak voltage value of 10 mV was applied between the counter copper plate and each of reference copper plates having varied surface areas to measure the intensity value of alternating current flowing therebetween. By graphing the relation between the surface areas and the electric capacity values, it was found that the proportion relation held for a surface area of up to at least 3 cm$^2$.

Copper plating was then slightly applied to a bolt that was a sample, the surface area of which was to be measured, and the measurement was carried out under the same conditions as already mentioned to obtain an electric capacity value. From that value, the bolt was found to have a surface area of 2.4 cm$^2$. By calculation from the graphical dimensions, however, the bolt was found to have a surface area of 2.48 cm$^2$.

EXAMPLE 2

With the same arrangement as used in Example 1 provided that a steel vessel was employed as the opposite electrode, the surface area of a bolt made of mild steel was measured.

The calculated surface area was 44.75 cm$^2$, whereas the measurement according to the method of the present invention was 44.5 cm$^2$ with the error being within 1%.

EXAMPLE 3

With the same arrangement as used in Example 2, the surface area of a perpendicularly bent copper plate was measured.

The calculated surface area was 200.0 cm$^2$, whereas the measurement according to the invented method was 201 cm$^2$, with the error being 1%.

As detailed above, the surface area-measuring method according to the present invention is characterized in that it is very simple and can rapidly be carried out by any person, and is also effective for the measurement of the surface area of articles of complicated profile or bodies of curved profile, and for the measurement of the inner surface areas of bodies which are not visually observable from the outside.

Since the arrangement for carrying out this method is not a special one, difficulty is not experienced in making measurements not only in laboratories but also on industrial sites. Rather, the results of surface area measurements obtained on industrial sites are immediately reflected in setting-up of operating conditions for surface treatments, thus making a great contribution to productivity.

What is claimed is:

1. A method for measuring the surface area of a body having an electrically conductive surface or a body coated on its surface with an electrically conductive material, comprising:

applying an alternating current voltage of from about 200 Hz to 50 KHz, with the peak value being between about 1 mV and 100 mV, between said body and a corrosion-resistant opposite electrode which are immersed in an electrically conductive solution having no corrosiveness upon the surface of said body to obtain an electric capacity value, and substituting said value in a function of a surface area and an electric capacity value obtained using a reference body having a known surface area in a similar manner.

2. A method as defined by claim 1, wherein said body and the reference body have electrically conductive surfaces formed of the same material.

* * * * *